United States Patent
Meyers

(10) Patent No.: US 7,246,902 B2
(45) Date of Patent: Jul. 24, 2007

(54) CORNEAL RESHAPING APPARATUS AND METHOD

(75) Inventor: William E. Meyers, Scottsdale, AZ (US)

(73) Assignee: Paragon Vision Sciences, Inc., Mesa, AZ (US)

( * ) Notice: Subject to any disclaimer, the term of this patent is extended or adjusted under 35 U.S.C. 154(b) by 0 days.

(21) Appl. No.: 10/906,599

(22) Filed: Feb. 25, 2005

(65) Prior Publication Data

US 2005/0213029 A1 Sep. 29, 2005

Related U.S. Application Data

(60) Provisional application No. 60/547,852, filed on Feb. 25, 2004.

(51) Int. Cl.
*G02C 7/04* (2006.01)

(52) U.S. Cl. .................... 351/160 R; 351/177

(58) Field of Classification Search ............ 351/159, 351/160 R, 177
See application file for complete search history.

(56) References Cited

U.S. PATENT DOCUMENTS

| | | | |
|---|---|---|---|
| 3,973,837 A * | 8/1976 | Page ..................... 351/160 R |
| 5,626,865 A * | 5/1997 | Harris et al. ............... 424/427 |
| 6,010,219 A * | 1/2000 | Stoyan .................. 351/160 R |
| 2005/0105047 A1 * | 5/2005 | Smitth et al. ............... 351/177 |

* cited by examiner

*Primary Examiner*—Scott J. Sugarman
*Assistant Examiner*—Darryl J. Collins
(74) *Attorney, Agent, or Firm*—Snell & Wilmer LLP

(57) ABSTRACT

The present invention includes systems and methods for improving vision by reshaping the cornea of an eye. The systems and methods include two or more contact lenses configured to be at least temporarily worn on the cornea at the same time, and to exert force on the cornea to change its shape. After the shape of the cornea has been appropriately changed, a contact lens with the appropriate configuration may be worn as needed to maintain the new shape of the cornea.

16 Claims, 1 Drawing Sheet

CORNEAL RESHAPING APPARATUS AND METHOD

CROSS-REFERENCE TO RELATED APPLICATIONS

This application claims priority to U.S. Provisional Application No. 60/547,852 filed Feb. 25, 2004, which provisional application, in its entirety, is hereby incorporated by reference.

FIELD OF INVENTION

This invention generally relates to devices and methods for reshaping the cornea of an eye.

BACKGROUND OF INVENTION

In the treatment of visual acuity deficiencies, correction by means of eyeglasses or contact lenses is used by a large percentage of the population. Such visual acuity deficiencies include hyperopia or far-sightedness, myopia or near-sightedness, astigmatisms (caused by asymmetry of a patient's eye) and presbyopia (caused by loss of accommodation by the crystalline lens). To alleviate the burden of wearing eyeglasses and/or contact lenses, surgical techniques have been developed for altering the shape of a patient's cornea in an attempt to correct refractive errors of the eye. Such surgical techniques include photorefractive keratectomy (PRK), LASIK (laser-assisted in-situ keratomileusis), as well as procedures such as automated lamellar keratoplasty (ALK) or implanted corneal rings, implanted contact lenses, and radial keratotomy (RK). These procedures are intended to surgically modify the curvature of the cornea to reduce or eliminate visual defects. The popularity of such techniques has increased greatly, but such techniques still carry risk in both the procedures themselves, as well as post-surgical complications.

Alternatives to permanent surgical procedures to alter the shape of the cornea include corneal refractive therapy (CRT) and orthokeratology (also known as "ortho-K"), in which a modified contact lens is applied to the eye to alter the shape or curvature of the cornea by compression of the corneal surface imparted by the corrective lens.

SUMMARY OF INVENTION

While the way in which the present invention addresses the disadvantages of the prior art will be discussed in greater detail below, in general, the present invention provides for the reshaping of the cornea of an eye to improve deficiencies in eyesight relating to conditions such as myopia, hyperopia, presbyopia, astigmatism and other visual acuity deficiencies. For example, in accordance with various embodiments of the present invention, a series of and/or combination of lenses (e.g., in layers) is placed on the cornea for varying periods of time. The contact lenses have various configurations which, over time, reshape the cornea and thus change the focus of light as it passes through the cornea, thereby allowing correction of various visual acuity deficiencies.

BRIEF DESCRIPTION OF THE DRAWINGS

The exact nature of this invention as well as its objects and advantages will be readily understood upon consideration of the following specification as related to the attendant drawings wherein like reference numeral throughout the drawings indicate like parts, and wherein.

DETAILED DESCRIPTION

Figure 1:
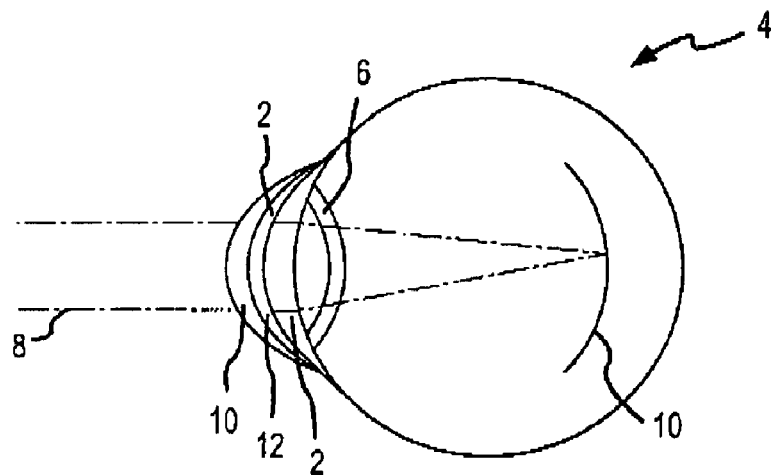
FIG. 1 is a perspective view of an embodiment of the present invention.
Figure 2:
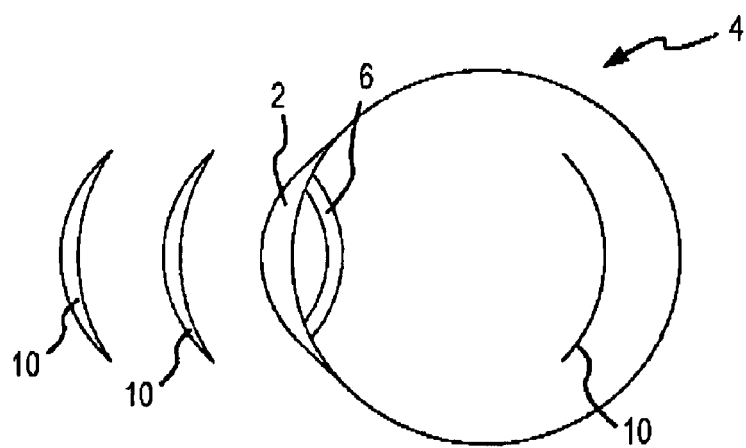
FIG. 2 is an exploded view of FIG. 1.

The following description is of exemplary embodiments of the invention only, and is not intended to limit the scope, applicability or configuration of the invention in any way. Rather, the following description is intended to provide a convenient illustration for implementing various exemplary embodiments of the invention. As will become apparent, various changes may be made in the function and arrangement of the elements described in these embodiments without departing from the scope of the invention as set forth in the appended claims. For example, the present invention is described below by referring to various "rigid" and "soft" lenses, as well as describing various time period ranges during which the various lenses are worn. However, it should be appreciated that such embodiments are non-limiting and that a variety of lenses, time periods and other elements fall within the ambit of the present invention.

The present invention generally provides for the reshaping of the cornea 2 of an eye 4 to improve deficiencies in eyesight relating to conditions such as myopia (near-sightedness), hyperopia (far-sightedness), presbyopia (gradual loss of the eye's ability to change focus for seeing near objects caused because of the lens becoming less elastic) astigmatism (distorted vision) and other such conditions caused by refractive errors in the eye 4. For proper eyesight, the cornea 2 (the clear window in front of the eye) and the lens 6 (behind the pupil) must properly focus or "refract" light 8 onto the retina 10 (at the back of the eye). If the length or shape of the eye is not ideal, the light may get focused too early or too late leaving a blurred image on the retina. For example, in the case of myopia, the eye is elongated (measuring from the front to the back of the eyeball) and in the case of hyperopia, the eye is shortened.

In accordance with various embodiments of the present invention, the cornea is reshaped to compensate for the elongation, shortening, and/or other irregularities of the eye. Such reshaping may be generally referred to herein as corneal refractive therapy or "CRT." For example, in accordance with one exemplary embodiment, a substantially rigid "contact" lens is placed on the eye in need of correction. Briefly, as used herein, a "rigid lens" is a lens which is relatively inflexible—it retains its shape both before and after placement on the cornea. A "soft lens" is a lens which, though it still retains its general shape, is relatively flexible and tends to conform to the cornea more so than a rigid lens. Thus, in general, because of its more flexible nature, a soft lens tends to be more comfortable to a user than a rigid lens. Note, however, as used herein, the terms "rigid" and "soft" should be understood generally as relative to one another. Stated another way, two different lenses both may be considered "rigid" or "soft" by industry standards, but when one lens is compared to the other, one has more predictability in reshaping the cornea (e.g., the rigid lens) and the other more flexibility and typically, a greater degree of comfort to the wearer (e.g., the soft lens).

Continuing on, the "rigid" lens has a shape designed to exert varying degrees of pressure on different areas of the cornea, for example, by varying the shape and thickness of varying portions of the lens. The shape of the rigid lens is determined based on the initial shape of the cornea, which is determined using methodologies and equipment now known or as yet unknown in the art, which measures the "topography" of the cornea.

Because of the semi-pliable nature of the cornea, the pressure from the rigid lens changes the shape of the cornea. Over time, the cornea tends to develop and retain (at least for some period of time) a new shape in reaction to the forces exerted by the lens, including after removal of the lens.

Individual corneas vary in terms of their resistance to or acceptance of reshaping. For example, a cornea may be more or less susceptible to reshaping based on its pliability, thickness, the amount of correction needed, and the like. Thus, the specific time period for which a rigid lens should be worn to achieve a desired result may be based on such factors. For example, the rigid lens may be worn from anywhere from 1 day to 30 days (or longer) and may be worn continuously or for intervals over the course of treatment with the rigid lens (e.g., every other day, for 12 hour periods, at night or while sleeping, etc.) based on the characteristics of the individual cornea and the nature of the desired result. Moreover, the treatment period may be adjusted based upon actual reshaping of the cornea proceeding at a faster or slower pace than initially predicted. Thus, in accordance with one aspect of an exemplary embodiment of the present invention, by appropriate selection of the shape of lens, the new shape of the cornea may be suitably predicted and controlled and vision deficiencies can be improved.

Similar dynamics result when using soft reshaping lenses, though typically, the results are less pronounced. That said, in accordance with the present invention, when combinations of rigid and soft lenses are used, either in layers or sequentially, beneficial aspects of both types of lenses can be realized.

For example, in accordance with one aspect of an exemplary embodiment of the present invention, a combination of rigid and/or soft lenses may be used simultaneously for correction in a layered or "piggyback" manner. For example, in one embodiment, the soft lens 12 is placed directly on the cornea 2. The posterior surface of the soft lens 12 is configured similar to that of a rigid lens 10, such as a rigid gas (RGP) permeable lens, and is worn under the rigid lens 10, to achieve reshaping. Once a desired shape is achieved, only the soft lens need be used to delay degradation of the desired shape.

In accordance with an alternative aspect of an exemplary embodiment of the present invention, three or more lenses may be layered (e.g., in a "sandwich" configuration) to treat visual acuity deficiencies. For example, in accordance with an exemplary embodiment, a rigid lens is placed between a soft lens—which contacts the cornea—and another lens (preferably a soft lens)—which contacts the inner surface of the eye lid. As such, comfort to the wearer may be increased. Additionally, as in the above embodiments, after a period of treatment with a "sandwich" lens configuration, only a soft lens need be used to slow degradation of the reshaping. That said, it should be appreciated that varying numbers of lenses and layers (e.g., 1, 2, 3, . . . n) of both rigid and soft lenses may be used in accordance with the present invention.

In some instances, after the cornea is reshaped using a rigid lens or a rigid/soft combination (piggyback or "sandwich" lens configuration), over time, the shape of the cornea gradually deforms from the shape imposed by the treatment. This occurs because the initial corneal reshaping primarily involves movement and flattening of the epithelial cells (of the epithelium—the thin, outer layer) of the cornea. Thus, in accordance with another aspect of an exemplary embodiment of the present invention, continuing treatment using a second lens, which causes the underlying Bowman's layer and the stromal bed (the thickest portions of the cornea) to take on the new shape, thus slowing the gradual deformation of the cornea that occurs after the initial rigid lens treatment. Moreover, the reshaping of the stroma tends to need less force to be maintained, and thus, the reshaping lasts longer.

For example, in accordance with one exemplary embodiment of the invention, preferably, a soft lens is used to slow degradation of the treatment (e.g., regression of the eye to its condition prior to reshaping). As with the rigid lens, selection of lens shape, the time period of treatment (including both length of time and treatment intervals etc.), and other specifications of treatment are preferably selected based upon characteristics of the individual cornea. As such, in accordance with one aspect of an exemplary embodiment of the present invention, the more comfortable soft lens thus can be used to maintain the corneal shape for longer periods than previously thought possible (e.g., instead of days or a few weeks, numerous weeks or months). By way of example, after a first period of treatment, a post-treatment map of the reshaped cornea may be taken and a difference map may be computed illustrating changes in the eye from its original, pre-treatment shape. A soft lens may then be fabricated based on the difference map. This soft lens is then worn (e.g., at night) to extend the time between rigid lens or rigid/soft lens combination treatments.

Further in accordance with various exemplary embodiments of the present invention, the treatments with the rigid lens and rigid lens/soft lens combination sequences may take any number of forms. For example, a rigid lens may be used exclusively for a period of time, followed by the exclusive use of a soft lens for a period of time. Alternatively, the rigid lens and soft lens treatments may be alternated periodically to achieve desired treatment objectives. For example, a rigid lens may be used during the day, while a soft lens may be used during the night (for comfort, etc.). In any event, such sequences should not be construed as limiting, but rather as exemplary of alternative sequences possible in accordance with various aspects of exemplary embodiments of the present invention.

Additionally, in accordance with further embodiments of the present invention, the lenses utilized may exaggerate the shape change in the difference map to further slow the regression of the initial treatment. Moreover, in accordance with additional aspects of the present invention, the lenses may also provide treatment for further visual anomalies, under-treatments or non-corneal astigmatism.

Additionally, in accordance with further aspects of the present invention, the lenses can be configured to provide additional desired refractive properties. For example, because in some instances, alterations in the geometry of the lens may be difficult to realize because of side effects on reshaping forces, the lens itself may be configured to adjust its optical power. For example, various diffractive optics may be used. By way of example, a diffractive pattern may be etched on the lens to yield corrective power.

Finally, it should be understood that various principles of the invention have been described in illustrative embodiments only, and that many combinations and modifications of the above-described structures, arrangements, proportions, elements, materials and components, used in the practice of the invention, in addition to those not specifically described, may be varied and particularly adapted to specific users and their requirements without departing from those principles. For example, as should be appreciated by one skilled in the art various combinations of layers and sequences of rigid and soft lenses, not expressly discussed herein, may be used and still fall within the ambit of the present invention.

What is claimed is:

1. A system to reshape the cornea of an eye, comprising:
a first contact lens; and
a second contact lens, wherein:
said first contact lens and said second contact lens are configured to reshape the cornea while being worn simultaneously on the eye,
said second contact lens is configured to be worn independently on the eye, and
said first contact lens is more rigid than said second contact lens.

2. The system of claim 1, wherein said first contact lens is a rigid contact lens.

3. The system of claim 1, wherein said second contact lens is a soft contact lens.

4. The system of claim 1, wherein said first contact lens is configured to exert varying degrees of pressure on different areas of the cornea when worn.

5. The system of claim 1, further comprising:
a third contact lens configured to be worn simultaneously with said first contact lens and said second contact lens.

6. The system of claim 5, wherein said third contact lens is one of a soft contact lens and a rigid contact lens.

7. The system of claim 5, wherein said first contact lens is configured to be worn between said second contact lens and said third contact lens.

8. The system of claim 1, further comprising:
at least two additional contact lenses, wherein each contact lens is configured to be worn simultaneously with each other, said first contact lens, and said second contact lens.

9. The system of claim 1, wherein said second contact lens is configured to at least partially contact the cornea and said first contact lens is configured to at least partially piggyback said second contact lens.

10. The system of claim 1, further comprising:
a third contact lens configured to be worn on the eye after the cornea has been at least partially reshaped by said first contact lens and said second contact lens to at least increase an amount of time the cornea remains reshaped.

11. The system of claim 10, wherein said third contact lens is one of a soft contact lens and a rigid contact lens.

12. The system of claim 1, wherein at least one of said first contact lens and said second contact lens is configured to yield a corrective power.

13. A method to at least temporarily improve vision comprising the step of:
reshaping at least a portion of a cornea of an eye to form a new shape utilizing at least a first contact lens, and a second contact lens configured to be worn independently on an eye:
wherein said first contact lens and said second contact lens are configured to reshape the cornea while being worn simultaneously; and
wherein said first contact lens is more rigid than said second contact lens.

14. The method of claim 13, wherein the reshaping step comprises the step of:
placing said first contact lens and said second contact lens on at least said portion of the cornea.

15. The method of claim 13, further comprising the step of:
exerting force on said portion of the cornea utilizing a third contact lens configured to at least temporarily maintain said new shape of said portion of the cornea.

16. The method of claim 15, wherein said exerting force step comprises the step of:
placing said third contact lens on at least said portion of the cornea.

* * * * *